(12) United States Patent
Vogt et al.

(10) Patent No.: US 8,512,762 B2
(45) Date of Patent: Aug. 20, 2013

(54) SPORICIDAL COMPOSITIONS AND USE THEREOF

(75) Inventors: Sebastian Vogt, Erfurt (DE); Hubert Büchner, Reinheim (DE)

(73) Assignee: Heraeus GmbH, Wehrheim (DE)

( * ) Notice: Subject to any disclaimer, the term of this patent is extended or adjusted under 35 U.S.C. 154(b) by 488 days.

(21) Appl. No.: 12/640,905

(22) Filed: Dec. 17, 2009

(65) Prior Publication Data
US 2010/0159027 A1    Jun. 24, 2010

(30) Foreign Application Priority Data

Dec. 18, 2008  (DE) .......................... 10 2008 063 524
Jan. 20, 2009  (DE) .......................... 10 2009 005 534

(51) Int. Cl.
*A01N 39/00*  (2006.01)
*A61K 33/40*  (2006.01)

(52) U.S. Cl.
USPC ........................................................ 424/615

(58) Field of Classification Search
None
See application file for complete search history.

(56) References Cited

FOREIGN PATENT DOCUMENTS

CN           101338173 B   *   7/2007

* cited by examiner

*Primary Examiner* — James H Alstrum Acevedo
*Assistant Examiner* — Thor Nielsen
(74) *Attorney, Agent, or Firm* — Norris McLaughlin & Marcus PA

(57) ABSTRACT

What is described are sporicidal compositions, in which hydrogen peroxide and at least one radical stabilizer are homogeneously dissolved in a methacrylate monomer or a mixture of methacrylate monomers, and the quantitative ratio of radical stabilizer to hydrogen peroxide is larger than or equal to 1 to 1. The sporicidal monomer/monomer mixture is usually used for producing single component bone cement pastes; two-component bone cement pastes or monomer solutions for polymethylmethacrylate bone cements that are based on cement powder and monomer liquid. Moreover, a sporicidal cement paste having the following components is proposed:
 hydrogen peroxide and/or a hydrogen peroxide-releasing substance or mixture of substances;
 radical stabilizer;
 low-molecular liquid methacrylate;
 linear or branched polymethylmethacrylate or linear or branched methylmethacrylate co-polymer;
 cross-linked polymethylmethacrylate or cross-linked methylmethacrylate copolymer; as well as
 at least one component of a radical initiator system.

7 Claims, No Drawings

SPORICIDAL COMPOSITIONS AND USE THEREOF

The subject matter of the invention are sporicidal compositions and the use thereof, in particular as or for the production of bone cement pastes.

PMMA bone cements (polymethylmethacrylate bone cements) have been known for decades and are based on the groundbreaking work of Sir Charnley (Charnley, J.: Anchorage of the femoral head prosthesis of the shaft of the femur. J. Bone Joint Surg. 42 (1960) 28-30). The basic structure of the PMMA bone cements has remained basically unchanged ever since. PMMA bone cements consist of a liquid monomer component and a powder component. The monomer component generally contains the monomer, methylmethacrylate, and an activator (N,N-dimethyl-p-toluidine) dissolved therein. The powder component consists of one or more polymers that are made by polymerization, preferably suspension polymerization, based on methylmethacrylate and co-monomers, such as styrene, methylacrylate or similar monomers, a radio-opaquer, and the initiator, dibenzoylperoxide. PMMA bone cements are medical products of class IIb or, if antibiotics are added, of class III. It is therefore necessary for the cements to be marketed exclusively in sterile condition packaged in double sterile packaging in order to ensure the safety of the patients. The powder components of most PMMA bone cements is sterilized by exposure to ethylene oxide. Sterilization of the powder component by exposure to gamma radiation is also common. The monomer liquid is rendered sterile by sterile filtration followed by aseptic filling technique. Due to its lipophilic and thus denaturing properties, the methylmethacrylate used for production of the monomer liquid is biocidal for most vegetative forms of microbial life. Microorganisms are not viable in anhydrous methylmethacrylate. Microbial life is always dependent on the availability of water. Aside from the vegetative forms of microorganisms, there are also generative forms such as endospores. They are generative resting forms of microorganisms and are formed by gram-positive bacteria, in particular of the *Bacillus* and *Clostridium* genera in order to be able to survive unfavorable living conditions. In their resting state, endospores have no active metabolism and possess a multi-layered spore coat that protects the spore core from most of the exposure to chemicals and other environmental influences. This renders endospores extremely resistant to exposure to heat and chemicals (Borick, P. M.: Chemical sterilizers. Adv. Appl. Microbiol. 10 (1968) 291-312; Gould, G. W.: Recent advances in the understanding of resistance and dormancy in bacterial spores. J. Appl. Bacteriol. 42 (1977) 297-309; Gould, G. W.: Mechanisms of resistance and dormancy. p. 173-209. In Hurst, A. and Gould, G. W. (ed.), The bacterial spore. vol. 2, Academic Press, Inc. New York, 1983). Due to their strong resistance features, endospores are used as bioindicators in the validation and control of the efficacy of sterilization processes. In this context it is presumed that inactivation of the spores reflects that all vegetative forms of microbial life have been killed. Endospores of gram-positive bacteria belong to international resistance class III. Resistance classes I include non-spore-forming bacteria and vegetative forms of spore formers and resistance class II includes spores that are killed within a few minutes in a stream of water vapor at 105° C. According to DAB 2008 (German pharmacopoeia), all microorganisms of resistance classes I-III must be killed and/or irreversibly inactivated during a sterilization.

Aside from physical sterilization processes such as gamma irradiation, electron irradiation, UV irradiation, heat sterilization, and autoclaving with superheated steam, chemical agents are also used for sterilization. These include ethylene oxide, formaldehyde, glutardialdehyde, ophthaldialdehyde, hypochlorite, chlorine dioxide, iodine, peracetic acid, and hydrogen peroxide. Ethylene dioxide has a sporicidal effect only in the presence of moisture. The aldehydes have similar efficacy. They are commonly used in the form of aqueous solutions or, in the case of formaldehyde, in the gaseous state. Chlorine-based agents are also very effective. However, they are disadvantageous in that chlorine-containing secondary products remain after the germs are killed. As strongly oxidizing agents, peracetic acid and hydrogen peroxide are also used in the form of aqueous solutions. Sterilization with gaseous hydrogen peroxide is also feasible. Both substances have bactericidal, fungicidal, virucidal, and sporicidal effects (Russell, A. D.: Bacterial spores and chemical sporocidal agents. Clin. Microbiol. Rev., vol. 3, no. 2 (1990) 99-119). Hydrogen peroxide is a relatively unstable compound that disintegrates slowly in aqueous solution to form oxygen and water. It has no mutagenic/cancerogenic properties. The success of chemical sterilization processes generally depends on the concentration of the chemical agent, the time of exposure, and the water activity.

Paste-like polymethylmethacrylate-based cements are a continued development of the polymethylmethacrylate bone cements. They also contain, aside from polymethylmethacrylate or polymethylmethacrylate copolymers, a radio-opaquer and methylmethacrylate as monomer and, if applicable, additional methacrylate monomers. No more than traces of water are present. Vegetative life forms of microorganisms cannot survive in the cement pastes due to the lipophilic denaturing properties of the methylmethacrylate and due to the, for the most part, absence of water. Resting endospores are capable of surviving in methacrylate monomers for extended periods of time without being inactivated. For this reason, it is necessary to ensure that all forms of microbial life, including resting endospores, are safely killed/inactivated in the cement pastes. Because of the methacrylate monomers contained therein, cement pastes cannot be sterilized by exposure to heat and steam or by gamma and X-ray irradiation, since these sterilization methods might induce radical polymerization of the monomers or, in the case of steam sterilization, hydrolysis. Neither is it feasible to use ethylene oxide. Ethylene oxide is incapable of penetrating into sealed, diffusion-tight film bags. Sterile filtration cannot be performed due to the high viscosity of cement pastes and the presence of opaquer and filler particles that are contained in the cement pastes. Aseptic production is an alternative. However, it is extremely expensive.

It was therefore the object of the invention to devise a reasonably priced, simple way of modifying monomers or monomer solutions such that these possess at least temporary sporicidal properties and thus to render the monomers or monomer solutions autosterile in order to be able to use them to produce, in particular, sterile cement pastes. It is also important for the monomers or monomer mixtures thus modified to be sufficiently stable and capable of being polymerized with conventional radical initiator systems.

The invention is based on the surprising observation that low quantities of aqueous hydrogen peroxide solution can be mixed homogeneously with methylmethacrylate or other methacrylate monomers and that these solutions possess sporicidal properties for a few days. It is also feasible to homogeneously dissolve gaseous hydrogen peroxide in methylmethacrylate or other methacrylate monomers. The methylmethacrylate remains stable by adding a stabilizer that is soluble in methylmethacrylate. In this context, an excess of stabilizer with respect to hydrogen peroxide is used. It was surprising in this context that the inactivation of endospores occurs despite the presence of stabilizers. The stabilizer is ultimately oxidized while consuming the hydrogen peroxide. The only side product aside from the oxidized stabilizer is water, which is non-toxic and present in traces. The essential advantage of this autosterile monomer/monomer mixture is that the cement pastes that are produced using it have sporicidal efficacy immediately after their production and for a period of several days. This allows the cement pastes to be sealed in suitable diffusion-tight composite film bags. The sealed cement paste irreversibly inactivates any microorganisms adhering to the inside of the composite film bags by means of oxidation. This means that the cement paste and the inside of the foil bag are sterilized by being exposed to the monomer/monomer mixture according to the invention. Extensive tests showed that a reduction of endospores by 6 log unit is safely attained. Another surprise was that the monomer mixtures according to the invention showed sporicidal efficacy even at extremely low hydrogen peroxide concentrations of 50 ppm.

The object of the invention is met by compositions according to claim 1. Further preferred embodiments are evident from claims 2-6. The invention also relates to the use of compositions according to the invention according to claim 7.

Component A

The term, methacrylate monomers, is generally understood to mean esters of methacrylic acid and aliphatic, cycloaliphatic, and aromatic alcohols, whereby the esters can also be formed with dialcohols, trialcohols or other polyalcohols. The most significant representative of these monomers is methylmethacrylate. The term, methacrylate monomer, is also understood to include methacrylic acid amide and singly N-substituted or doubly N,N-substituted methacylic acid amides.

Component B

Hydrogen peroxide is usefully added to the compositions in the form of a 30% solution. Hydrogen peroxide can be released in situ from suitable hydrogen peroxide adducts. For example, it is feasible to release hydrogen peroxide in situ from alkaline earth peroxides or alkali peroxides by exposure to acids that are soluble in methacrylate monomers. Possible organic acids, aside from 2-ethylhexanoic acid and methacrylic acid, include all organic acids that are soluble in methacrylate monomers and whose alkali and alkaline earth salts are also soluble in methacrylate monomers. The addition of hydrogen peroxide derivatives such as peracetic acid, performic acid, perpropionic acid, perphthalic acid, perbenzoic acid, and 3-chloroperbenzoic acid is also within the scope of the invention. In this context, for attainment of optimal sporicidal effect it is advantageous to add traces of water to the monomer/monomer mixture. The person skilled in the art is aware of further suitable hydrogen peroxide-releasing substances or mixtures of substances. Preferred substances of this type include hydrogen peroxide-urea adduct and sodium carbonate-hydrogen peroxide adduct; preferred mixtures include the combinations, sodium carbonate-hydrogen peroxide adduct/2-ethylhexanoic acid, calcium peroxide/2-ethylhexanoic acid, as well as magnesium peroxide/2-ethylhexanoic acid.

Component C

Possible radical stabilizers include all stabilizing compounds that are used as radical stabilizers in polymer chemistry. They should be effective as reducing agent and be capable of reacting with radicals. The stabilizers must be capable of binding oxygen. Preferred examples of stabilizers of this type are hydroquinone, hydroquinone monomethylether, palmitoylascorbic acid, 2,6-di-t-butyl-4-methylphenol (BHT), and alkyl gallates.

It is essential for the invention that the quantitative ratio of radical stabilizer to hydrogen peroxide is larger than or equal to 1 to 1. This ensures that the radicals that are released during disintegration of the hydrogen peroxide are safely scavenged and spontaneous polymerization of the monomer/monomer mixture is prevented. Another reason for the radical stabilizer to always be present at an at least equimolar quantitative ratio with respect to hydrogen peroxide is that the oxygen that is released upon disintegration of hydrogen peroxide gets bound and no oxygen bubbles can form in the monomer/monomer mixture. The hydrogen peroxide or the released hydrogen peroxide and the radical stabilizer are homogeneously dissolved in the monomer or monomer mixture.

The hydrogen peroxide concentration in the monomer/monomer mixture preferably is 20 ppm to 0.5%, particularly preferred up to 0.01%, with respect to the mass of the monomer or monomer mixture.

The compositions according to the invention are preferably used for producing single component bone cement pastes, two-component bone cement pastes or monomer solutions for polymethylmethacrylate bone cements that are based on cement powder and monomer liquid.

A particularly preferred composition contains the components,

A1 a low-molecular liquid methacrylate;
A2 a linear or branched polymethylmethacrylate or a linear or branched methylmethacrylate copolymer;
A3 a cross-linked polymethylmethacrylate or a cross-linked methylmethacrylate copolymer;
B1 hydrogen peroxide and/or
B2 a hydrogen peroxide-releasing substance or a hydrogen peroxide-releasing mixture of substances;
C at least one radical stabilizer; and
D at least one component of a radical initiator system.

It can be used as the base of a sporicidal cement paste that can, in addition, contain pharmaceutical agents and growth factors, such as, e.g., antibiotics, antiphlogistic agents, cytostatic agents, immunomodulators, bisphosphonates, steroid hormones, BMP (bone morphogenetic proteins). Moreover, zirconium dioxide, barium sulfate, iodine-organic radioopaquer, tantalum, and tungsten as radio-opaquer can be incorporated into the cement paste. In addition, it is also feasible to suspend superparamagnetic nanoparticles and ferromagnetic particles in the cement paste. These particles can be used to heat the cement paste by exposure to alternating magnetic fields, whereby the radical polymerization and thus the curing of the cement paste can be induced by means of the disintegration of thermally disintegrating initiators.

The invention is illustrated in more detail by the examples presented in the following without limiting the scope of the invention. Like in the other parts of the description, any specification of parts and percentages refers to the weight unless specified otherwise.

1. Production and Testing of sporicidal methylmethacrylate Solutions 30 mg 2,6-di-t-butyl-4-methylphenol and 50 µl, 25 µl, 10 µl, and 5 µl 30% hydrogen peroxide solution were dissolved in 50.0 g methylmethacrylate each. Five spore-strips (Sterix) containing $3 \times 10^6$ *Bacillus atropheus* (*Bacillus subtilis*) spores were added to each of the solutions. A solution containing 60.0 g methylmethacrylate and 30 mg 2,6-di-t-butyl-4-methyl-phenol containing no hydrogen peroxide was used as control. The solutions were incubated at 37° C. for three days. Subsequently, the spore-strips were removed and dried at room temperature. For the determination of the viable spore content, the spores were rinsed from the spore-strips, incubated, and then quantified.

| Volume of 30% hydrogen peroxide solution added | Viable spores per spore-strip (mean of 5 spore-strips) |
|---|---|
| — | $3 \times 10^5$ |
| 50 µl | 0 |
| 25 µl | 0 |
| 10 µl | 0 |
| 5 µl | 0 |

2. Production and Testing of sporicidal Two-Component Cement Pastes

Two-component paste cements with components A and B were produced. Components A and B each were produced by simple mixing of the raw materials at room temperature.

| Composition | |
|---|---|
| Component A | Component B |
| 3.0 g zirconium dioxide | 3.0 g zirconium dioxide |
| 15.0 g methylmethacrylate | 15.0 g methylmethacrylate |
| 10.0 g polymethylmethacrylate | 10.0 g polymethylmethacrylate |
| 9.0 g cross-linked polymethylmethacrylate | 9.0 g cross-linked polymethylmethacrylate |
| 1.0 g 1-cyclohexyl-5-ethyl-barbituric acid | 0.5 g trioctylmethylammonium chloride |
| 30 mg 2,6-di-t-butyl-4-methyl-phenol | 100 ppm copper(II) octoate |
| | 30 mg 2,6-di-t-butyl-4-methyl-phenol |

Component A was mixed with 10 µl or 5 µl 30% hydrogen peroxide solution. Component B was also mixed with 10 µl or 5 µl 30% hydrogen peroxide solution. Five spore-strips (Sterix) containing $3 \times 10^6$ Bacillus atropheus (*Bacillus subtilis*) spores were added to each of the homogeneous cement pastes. Cement pastes A and B without hydrogen peroxide being added were run as controls. Incubation at 37° C. was performed for three days. Subsequently, the spore-strips were removed and dried at room temperature. For the determination of the viable spore content, the spores were rinsed from the spore-strips, incubated, and then quantified.

| Volume of 30% hydrogen peroxide solution added | Viable spores per spore-strip (mean of 5 spore-strips) | |
|---|---|---|
| | Paste A | Paste B |
| — | $3 \times 10^5$ | $3 \times 10^5$ |
| 10 µl | 0 | 0 |
| 5 µl | 0 | 0 |

Subsequently, the mechanical properties of cement produced from the hydrogen peroxide-modified pastes A and B were determined. For this purpose, the hydrogen peroxide-modified pastes A and B were mixed at a weight ratio of 1:1 and subsequently placed in rectangular molds having a height of 3.2 mm. After curing was complete, strips having a length of 75 mm and a width of 10 mm were sawed to test the 4-point flexural strength test and the flexural modulus. In addition, test bodies having a length of 20 mm and a width of 10 mm were sawed to test the dynstat flexural strength and impact strength. The test of 4-point flexural strength and flexural modulus was performed after storage of the test bodies in water at 37° C. for 48 hours using a Zwick-Universal testing apparatus. The dynstat flexural strength and the dynstat impact strength were determined after storage of the test bodies at 23° C. exposed to air for 24 hours.

| Formulation | 4-point flexural strength [MPa] | Flexural modulus [MPa] | Dynstat flexural strength [MPa] | Dynstat impact strength [kN/m²] |
|---|---|---|---|---|
| Pastes A + B each containing 10 µl hydrogen peroxide solution | 67.8 ± 1.5 | 2698 ± 39 | 86.1 ± 5.7 | 4.07 ± 0.28 |
| Pastes A + B each containing 5 µl hydrogen peroxide solution | 65.8 ± 1.0 | 2494 ± 27 | 90.4 ± 5.4 | 3.17 ± 0.06 |

3. Production of a sporicidal One-Component Cement Paste

A one-component cement paste was produced by simple mixing at room temperature of the raw materials listed below. A brownish, viscous paste that was easy to shape and carve was thus produced.

| Composition of the cement paste |
|---|
| 2.0 g zirconium dioxide |
| 1.0 g magnetite particles |
| 15.0 g methylmethacrylate |
| 10.0 g polymethylmethacrylate |
| 9.0 g cross-linked polymethylmethacrylate |
| 50 mg α,α-azobis(isobutyronitrile) (AIBN) |
| 30 mg 2,6-di-t-butyl-4-methyl-phenol |
| 10 µl 30% hydrogen peroxide solution |

The cement paste was cured using an induction heating adopted from conventional induction cooking stoves (coil with control electronics, frequency 25 kHz). The polymerization commenced after approx. 60 seconds and produced stable molded bodies.

4. Production of a sporicidal One-Component Cement Paste

A one-component cement paste was produced by simple mixing at room temperature of the raw materials listed below. A brownish, viscous paste that was easy to shape and carve was thus produced.

| Composition of the cement paste |
|---|
| 2.0 g zirconium dioxide |
| 1.0 g magnetite particles |
| 15.0 g methylmethacrylate |
| 10.0 g polymethylmethacrylate |
| 9.0 g cross-linked polymethylmethacrylate |
| 50 mg α,α-azobis(isobutyronitrile) (AIBN) |
| 30 mg 2,6-di-t-butyl-4-methyl-phenol |
| 50 mg urea-hydrogen peroxide adduct |
| 50 µl water |

The cement paste was cured using an induction heating adopted from conventional induction cooking stoves (coil with control electronics, frequency 25 kHz). The polymerization commenced after approx. 60-70 seconds and produced stable molded bodies.

The invention claimed is:

1. A sporicidal composition comprising:
   A a methacrylate monomer or a mixture of methacrylate monomers;
   B1 hydrogen peroxide or
   B2 a hydrogen peroxide-releasing substance or a hydrogen peroxide-releasing mixture of substances; and
   C at least one radical stabilizer;
   whereby component B1 and the hydrogen peroxide released from component B2 as well as component C are homogeneously dissolved in component A; and
   the quantitative ratio of C to (B1+B2) is larger than or equal to 1 to 1 [mol/mol].

2. The sporicidal composition according to claim 1, wherein the hydrogen peroxide-releasing substances are selected from the group consisting of
   hydrogen peroxide-urea adduct and
   sodium carbonate-hydrogen peroxide adduct and the hydrogen peroxide-releasing mixtures of substances are selected from the group consisting of
   sodium carbonate-hydrogen peroxide adduct /2-ethylhexanoic acid;
   calcium peroxide/2-ethylhexanoic acid, and
   magnesium peroxide/2-ethylhexanoic acid.

3. The sporicidal composition according to claim 1, wherein the hydrogen peroxide is present in an amount of 20 ppm to 0.5 wt %, with respect to the monomer or mixture of monomers.

4. The sporicidal composition according to claim 3, wherein the hydrogen peroxide is present in an amount of 20 ppm to 0.01 wt %.

5. The sporicidal composition according to claim 1, wherein the stabilizer C is selected from the group consisting of hydroquinone, hydroquinone monomethylether, alkyl gallates, palmitoylascorbic acid, and 2,6-di-t-butyl-4-methylphenol.

6. The sporicidal composition consisting of
   A1 a low-molecular liquid methacrylate;
   A2 a linear or branched polymethylmethacrylate or a linear or branched methylmethacrylate copolymer;
   A3 a cross-linked polymethylmethacrylate or a cross-linked methylmethacrylate copolymer;
   B1 hydrogen peroxide or
   B2 a hydrogen peroxide-releasing substance or a hydrogen peroxide-releasing mixture of substances;
   C at least one radical stabilizer; and
   D at least one component of a radical initiator system.

7. A sporicidal composition consisting of
   A1 a low-molecular liquid methacrylate;
   A2 a linear or branched polymethylmethacrylate or a linear or branched methylmethacrylate copolymer;
   A3 a cross-linked polymethylmethacrylate or a cross-linked methylmethacrylate copolymer;
   B1 hydrogen peroxide or
   B2 a hydrogen peroxide-releasing substance or a hydrogen peroxide-releasing mixture of substances;
   C at least one radical stabilizer; and
   D at least one component of a radical initiator system,
   whereby component B1 and the hydrogen peroxide released from component B2 as well as component C are homogeneously dissolved in component A; and
   the quantitative ratio of C to (B1+B2) is larger than or equal to 1 to 1 [mol/mol].

* * * * *